(12) United States Patent
Ikeda et al.

(10) Patent No.: US 8,772,733 B2
(45) Date of Patent: Jul. 8, 2014

(54) CHARGED PARTICLE ACCELERATOR AND PARTICLE BEAM THERAPY SYSTEM

(75) Inventors: Masahiro Ikeda, Chiyoda-ku (JP); Yuko Kijima, Okayama (JP); Shunsuke Okada, Chiyoda-ku (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 16 days.

(21) Appl. No.: 13/582,645

(22) PCT Filed: Jan. 26, 2012

(86) PCT No.: PCT/JP2012/051597
§ 371 (c)(1),
(2), (4) Date: Sep. 4, 2012

(87) PCT Pub. No.: WO2013/111292
PCT Pub. Date: Aug. 1, 2013

(65) Prior Publication Data
US 2013/0193353 A1    Aug. 1, 2013

(51) Int. Cl.
*H01J 3/14* (2006.01)
*A61N 5/00* (2006.01)
(52) U.S. Cl.
USPC .............. 250/396 ML; 250/492.1; 250/492.3
(58) Field of Classification Search
USPC ............................ 250/492.3, 492.1, 396 ML
See application file for complete search history.

(56) References Cited

U.S. PATENT DOCUMENTS

| | | | |
|---|---|---|---|
| 5,280,239 A * | 1/1994 | Klimovitsky et al. | ... 324/207.26 |
| 7,071,466 B2 * | 7/2006 | Glukhoy | 250/287 |
| 7,122,978 B2 * | 10/2006 | Nakanishi et al. | 315/500 |
| 7,148,472 B2 * | 12/2006 | Glukhoy | 250/287 |
| 8,084,965 B2 * | 12/2011 | Takayama et al. | 315/503 |
| 2003/0136917 A1 * | 7/2003 | Woodburn et al. | 250/396 ML |
| 2009/0195194 A1 * | 8/2009 | Takayama et al. | 315/503 |

FOREIGN PATENT DOCUMENTS

| | | |
|---|---|---|
| JP | 7-192900 A | 7/1995 |
| JP | 8-293399 A | 11/1996 |
| JP | 10-294200 A | 11/1998 |
| JP | 2000-277770 A | 10/2000 |

OTHER PUBLICATIONS

International Search Report (PCT/ISA/210) issued on Feb. 28, 2012, by the Japanese Patent Office as the International Searching Authority for International Application No. PCT/JP2012/051597.

* cited by examiner

*Primary Examiner* — Nikita Wells
*Assistant Examiner* — Johnnie L Smith
(74) *Attorney, Agent, or Firm* — Buchanan Ingersoll & Rooney PC

(57) ABSTRACT

The objective is to obtain a charged particle accelerator where the amount of pattern data for operating an acceleration cavity and electromagnets based on time clocks is reduced and the pattern data communication time is shortened. An accelerator control apparatus provided in a charged particle accelerator of the present invention is characterized by including a clock generation unit that generates an acceleration cavity clock and an electromagnet clock that is synchronized with the acceleration cavity clock and has a frequency lower than that of the acceleration cavity clock; a high-frequency control unit that controls an acceleration cavity, based on an acceleration cavity pattern stored in a first pattern memory and the acceleration cavity clock; and a deflection electromagnet control unit that controls a deflection electromagnet, based on a deflection electromagnet pattern stored in a second pattern memory and the electromagnet clock.

20 Claims, 6 Drawing Sheets

CHARGED PARTICLE ACCELERATOR AND PARTICLE BEAM THERAPY SYSTEM

TECHNICAL FIELD

The present invention relates to a particle beam therapy system that is utilized in the medical field.

BACKGROUND ART

In general, a particle beam therapy system is provided with a beam generation apparatus that generates a charged particle beam; an accelerator that is connected with the beam generation apparatus and accelerates a generated charged particle beam; a beam transport system that transports a charged particle beam that is accelerated by the accelerator so as to gain predetermined energy and then emitted; and a particle beam irradiation apparatus, disposed at the downstream side of the beam transport system, for irradiating a charged particle beam onto an irradiation subject.

As an accelerator for accelerating a charged particle beam, for example, a synchrotron is utilized. A high-frequency wave is applied to a high-frequency acceleration cavity (acceleration cavity) provided in a synchrotron; pattern operation is implemented with a deflection electromagnet, and a quadrupole magnet, and the like synchronized with the high-frequency wave; then, a charged particle beam is accelerated so as to gain predetermined energy. In this situation, because the charged particle beam is made to circulate in a single and the same orbit, the circulation frequency becomes higher in proportion to the level of acceleration of the charged particle beam. Therefore, it is required to raise the acceleration frequency of an acceleration voltage, in proportion to the level of acceleration of a charged particle beam. That is to say, it is required to synchronize the magnetic field B of the deflection electromagnet with the acceleration frequency f of the acceleration voltage.

A conventional art in Patent Document 1 discloses a charged particle accelerator in which by use of a T-clock (time clock), a pattern for a deflection electromagnet is outputted so as to operate the deflection electromagnet; a B-clock (magnetic-field clock) is created based on a magnetic-field change observed with a magnetic-field measurement instrument provided in a reference electromagnet that is operated with the pattern for a deflection electromagnet; then, by use of the B-clock, a pattern for an acceleration cavity is outputted so as to activate a high-frequency acceleration cavity. In a conventional charged particle accelerator, a T-clock and a B-clock are utilized, as described above, so that the deflection electromagnet is synchronized with the high-frequency acceleration cavity. In this operation method, the T-clock and the B-clock, i.e., two clocks are utilized; therefore, the apparatus is complex. Thus, Patent Document 1 proposes a charged particle accelerator in which by utilizing only a T-clock, the pattern for a deflection electromagnet and the pattern for an acceleration cavity are outputted, and the deflection electromagnet and the high-frequency acceleration cavity are operated.

PRIOR ART REFERENCE

Patent Document

[Patent Document 1] Japanese Patent Application Laid-Open No. H08-293399 (Paragraphs 0008 through 0017, and FIGS. 1 and 3)

DISCLOSURE OF THE INVENTION

Problem(s) to be Solved by the Invention

In the case where the deflection electromagnet and the high-frequency acceleration cavity are operated by use only a T-clock, the amount of pattern data to be dealt with by the overall charged particle accelerator is extremely large; as a result, there has been a problem that the amount of hard disks or memories for storing the data becomes massive or that it takes a long time to perform communication of the pattern data. The amount of pattern data will be explained in detail below.

In general, a high-frequency wave of 10 MHz or lower is applied to the high-frequency acceleration cavity. A high-frequency acceleration cavity has a high tracking capability for a temporal change and is sensitive to the acceleration or deceleration of a beam; thus, the output frequency of the pattern clock needs to be at least 100 kHz. Furthermore, in the case where the high-frequency acceleration cavity is operated in such a way as to change smoothly, the frequency of the pattern output needs to be as high as 1 MHz. In contrast, because being formed by winding a coil around an iron core, a electromagnet such as a deflection electromagnet or a quadrupole electromagnet has a large reactance component and hence a large time constant; therefore, it may be allowed that the frequency of the operation pattern is 24 times as high as the frequency of the commercial power source (50 Hz or 60 Hz), i.e., as high as 1200 Hz or 1440 Hz. In the case where the two apparatuses having different temporal responsivenesses, i.e., the high-frequency acceleration cavity and the electromagnet are operated with a single and the same clock, it is required to synchronize the clock with the pattern output for the high-frequency acceleration cavity that has a higher temporal resolution. Accordingly, it is also required to output a rapid pattern of approximately 1 MHz so as to operate a slow-response electromagnet; thus, as described above, the amount of pattern data to be dealt with by the overall charged particle accelerator becomes extremely large.

With regard to the charged particle accelerator in Patent Document 1, as an example of electromagnet, only a deflection electromagnet is described; however, in practice, electromagnets for performing pattern operation include a convergence quadrupole electromagnet, a divergence quadrupole electromagnet, a convergence sextuple electromagnet, a divergence sextuple electromagnet, an orbit correction steering electromagnet (X direction/Y direction), an extraction sextuple electromagnet, and the like; in many cases, there exist ten to twenty kinds of electromagnets; because as the number of electromagnets, the patterns for controlling which are different from one another, increases, the data for those patterns increases, the increase in the amount of pattern data is a big problem; therefore, reduction of the amount of pattern data is an important issue.

The present invention has been implemented in order to solve the foregoing problems; the objective thereof is to obtain a charged particle accelerator in which the amount of pattern data for operating an acceleration cavity and electromagnets based on time clocks is reduced and the communication time for the pattern data is shortened.

Means for Solving the Problems

A charged particle accelerator according to the present invention includes a vacuum duct through which a charged particle beam passes; an acceleration cavity that accelerates a charged particle beam passing through the vacuum duct; a deflection electromagnet that deflects a charged particle beam passing through the vacuum duct; and an accelerator control apparatus that controls the acceleration cavity and the deflection electromagnet. The accelerator control apparatus is characterized by including a clock generation unit that generates an acceleration cavity clock and an electromagnet clock that is synchronized with the acceleration cavity clock and has a frequency lower than that of the acceleration cavity clock; a high-frequency control unit that controls the acceleration cavity, based on an acceleration cavity pattern stored in a first pattern memory and the acceleration cavity clock; and a deflection electromagnet control unit that controls the deflection electromagnet, based on a deflection electromagnet pattern stored in a second pattern memory and the electromagnet clock.

Advantage of the Invention

In a charged particle accelerator according to the present invention, an acceleration cavity and a deflection electromagnet are controlled by use of an acceleration cavity clock and an electromagnet clock that is synchronized with the acceleration cavity clock and has a frequency lower than that of the acceleration cavity clock; therefore, it is made possible to make the data amount of the deflection electromagnet pattern smaller than that of the acceleration cavity pattern; thus, the time for the communication of the pattern data with the accelerator can be shortened.

BEST MODE FOR CARRYING OUT THE INVENTION

Embodiment 1

Figure 1:
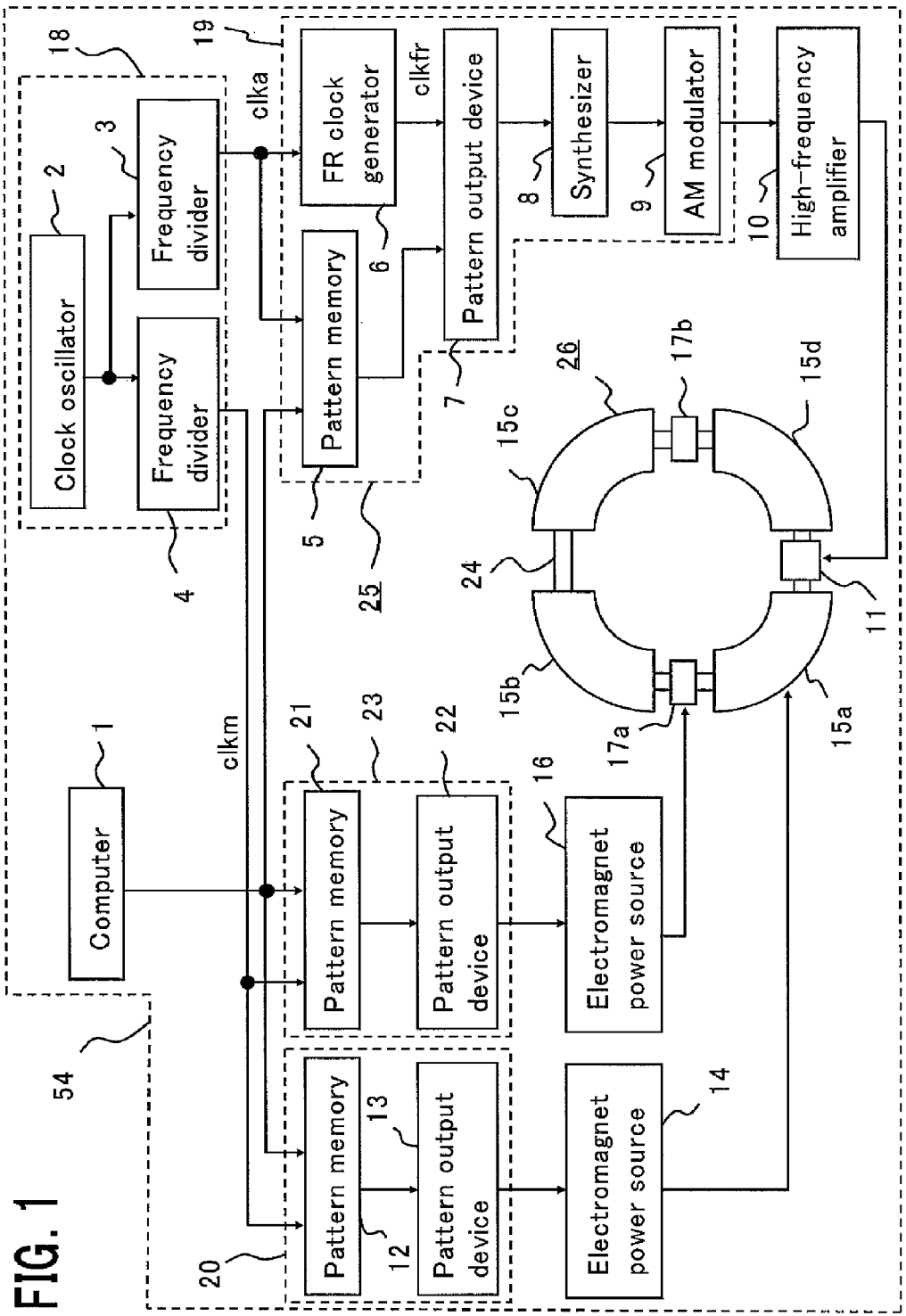
FIG. 1 is a diagram illustrating the configuration of a charged particle accelerator according to Embodiment 1 of the present invention.
Figure 2:
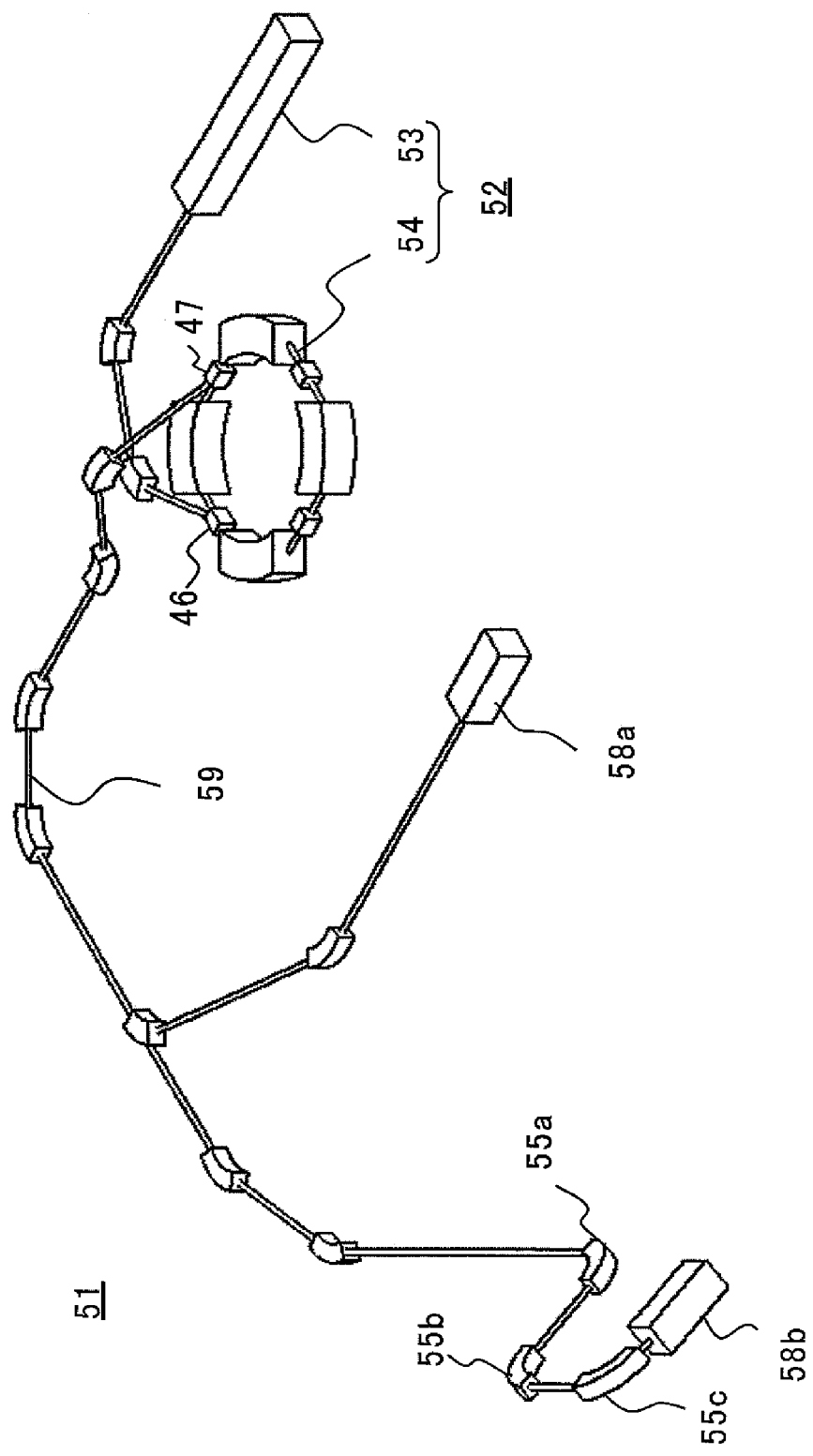
FIG. 2 is a schematic configuration diagram illustrating a particle beam therapy system according to Embodiment 1 of the present invention.
Figure 3:
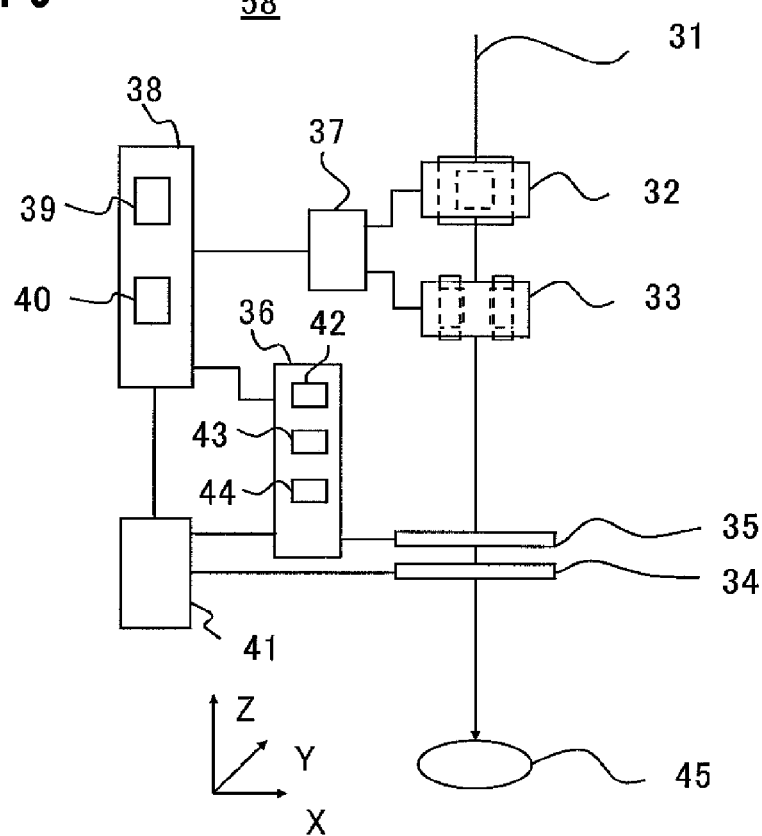
FIG. 3 is a diagram illustrating the configuration of a particle beam irradiation apparatus in FIG. 2.

FIG. 1 is a diagram illustrating the configuration of a charged particle accelerator according to Embodiment 1 of the present invention. FIG. 2 is a schematic configuration diagram illustrating a particle beam therapy system according to Embodiment 1 of the present invention; FIG. 3 is a diagram illustrating the configuration of a particle beam irradiation apparatus according to Embodiment 1 of the present invention. In FIG. 2, a particle beam therapy system 51 includes a beam generation apparatus 52, a beam transport system 59, and particle beam irradiation apparatuses 58a and 58b. The beam generation apparatus 52 includes an ion source (unillustrated), a prestage accelerator 53, and a charged particle accelerator 54. The particle beam irradiation apparatus 58b is provided in a rotating gantry (unillustrated). The particle beam irradiation apparatus 58a is provided in a treatment room where no rotating gantry is installed. The function of the beam transport system 59 is to achieve communication between the charged particle accelerator 54 and the particle beam irradiation apparatuses 58a and 58b. Part of the beam transport system 59 is provided in the rotating gantry (unillustrated), and that part includes a plurality of deflection electromagnets 55a, 55b, and 55c.

A charged particle beam, which is a particle beam such as a proton beam generated in the ion source, is accelerated by the prestage accelerator 53 and injected into the charged particle accelerator 54 through an injector 46. In this Description, the charged particle accelerator 54 will be explained with a synchrotron as an example. The particle beam is accelerated to gain predetermined energy. The charged particle beam launched from a launching apparatus 47 of the charged particle accelerator 54 is transported to the particle beam irradiation apparatuses 58a and 58b by way of the beam transport system 59. The particle beam irradiation apparatuses 58a and 58b each irradiate the charged particle beam onto an irradiation subject 45 (refer to FIG. 3). As the reference numeral of the particle beam irradiation apparatus, "58" is collectively utilized; however, in the case where the apparatuses are separately explained, "58a" and "58b" are utilized.

A charged particle beam 31 generated in the beam generation apparatus 52 and accelerated to gain predetermined energy is led to the particle beam irradiation apparatus 58 by way of the ion beam transport system 59. In FIG. 3, the particle beam irradiation apparatus 58 is provided with X-direction and Y-direction scanning electromagnets 32 and 33 that scan the charged particle beam 31 in the X direction and the Y direction, respectively, which are directions perpendicular to the charged particle beam 31; a position monitor 34; a dose monitor 35; a dose data converter 36; a beam data processing device 41; a scanning electromagnet power source 37; and an irradiation management apparatus 38 that controls the particle beam irradiation apparatus 58. The irradiation management apparatus 38 is provided with an irradiation control computer 39 and an irradiation control apparatus 40. The dose data converter 36 is provided with a trigger generation unit 42, a spot counter 43, and an inter-spot counter 44. The traveling direction of the charged particle beam 31 is −Z direction.

The X-direction scanning electromagnet 32 scans the charged particle beam 31 in the X direction, and Y-direction scanning electromagnet 33 scans the charged particle beam 31 in the Y direction. The position monitor 34 detects beam information for calculating the passing position (gravity center position) through which the charged particle beam 31 that has been scanned by the X-direction scanning electromagnet 32 and the Y-direction scanning electromagnet 33 passes and the size of the charged particle beam 31. The beam data processing device 41 calculates the passing position (gravity center position) and the size of the charged particle beam 31, based on beam information including a plurality of analogue signals (beam information items) detected by the position monitor 34. Moreover, the beam data processing device 41 generates an abnormality detection signal indicating a positional abnormality or a dimensional abnormality of the charged particle beam 31 and outputs the abnormality detection signal to the irradiation management apparatus 38.

The dose monitor 35 detects the dose of the charged particle beam 31. The irradiation management apparatus 38 controls the irradiation position of the charged particle beam 31 on the irradiation subject 45, based on treatment plan data created by an unillustrated treatment planning apparatus; when the dose measured by the dose monitor 35 and converted into digital data by the dose data converter 36 reaches the desired dose, the charged particle beam 31 is stopped. The scanning electromagnet power source 37 changes setting currents for the X-direction scanning electromagnet 32 and the Y-direction scanning electromagnet 33, based on control inputs (commands), which are outputted from the irradiation management apparatus 38, to the X-direction scanning electromagnet 32 and the Y-direction scanning electromagnet 33.

In this Description, the scanning irradiation method for the particle beam irradiation apparatus 58 will be explained assuming that it is the raster-scanning irradiation method in which when the irradiation position of the charge particle beam 31 is changed, the charged particle beam 31 is not stopped, i.e., it is a method in which as is the case with the spot scanning irradiation method, the beam irradiation position travels through spot positions one after another. The spot counter 43 measures the irradiation dose for a time during which the beam irradiation position of the charged particle beam 31 is stopped. The inter-spot counter 44 measures the irradiation dose for a time during which the beam irradiation position of the charged particle beam moves. The trigger generation unit 42 generates a dose completion signal when the dose of the charged particle beam 31 at the beam irradiation position reaches the desired irradiation position.

In FIG. 1, the charged particle accelerator 54 includes an acceleration ring 26, an accelerator control apparatus 25, a high-frequency amplifier 10, and electromagnet power sources 14 and 16. The acceleration ring 26 is provided with a vacuum duct 24 through which the charged particle beam 31 passes; four deflection electromagnets 15a, 15b, 15c, and 15d that supplies magnetic fields to the charged particle beam 31 passing through the vacuum duct 24 so as to deflect the charged particle beam 31; two quadrupole electromagnets 17a and 17b that supplies magnetic fields to the charged particle beam 31 passing through the vacuum duct 24 so as to make the charged particle beam 31 have a predetermined beam size; and an acceleration cavity 11 that accelerates the charged particle beam 31 passing through the vacuum duct 24. The accelerator control apparatus 25 includes a computer 1, a clock generation unit 18, a high-frequency control unit 19, a deflection electromagnet control unit 20, and a quadrupole electromagnet control unit 23. As the reference numeral of the deflection electromagnet, "15" is collectively utilized; however, in the case where the deflection electromagnets are separately explained, "15a", "15b", "15c", and "15d" are utilized. Similarly, as the reference numeral of the quadrupole electromagnet, "17" is collectively utilized; however, in the case where the quadrupole electromagnets are separately explained, "17a" and "17b" are utilized. The injector 46 that injects the charged particle beam 31 from the prestage accelerator 53 to the vacuum duct 24, the launching apparatus 47 that launches the charged particle beam 31 from the vacuum duct 24 to the beam transport system 59, and the like are omitted in FIG. 1.

The deflection electromagnet 15 generates a magnetic field for deflecting the charged particle beam 31 so as to make it circulate in the vacuum duct 24. The quadrupole electromagnet 17 generates a magnetic field for making a beam diverge or converge. The high-frequency amplifier 10 generates a high-frequency acceleration voltage, based on a control signal outputted from the high-frequency control unit 19. The electromagnet power source 14 generates a control current, based on a control signal outputted from the deflection electromagnet control unit 20. The electromagnet power source 16 generates a control current, based on a control signal outputted from the quadrupole electromagnet control unit 23. While establishing predetermined synchronization, the acceleration cavity 11, the deflection electromagnet 15, and the quadrupole electromagnet 17 accelerate, deflect, diverge, and converge the charged particle beam 31 so that the charged particle beam 31 is accelerated to gain predetermined energy.

The clock generation unit 18 includes a clock oscillator 2, a frequency divider 3 that generates an acceleration cavity clock clka, and a frequency divider 4 that generates an electromagnet clock clkm. The high-frequency control unit 19 includes a pattern memory 5, an FR clock generator 6 that generates an FR clock clkfr, a pattern output device 7, a synthesizer 8, and an AM modulator 9. The deflection electromagnet control unit 20 includes a pattern memory 12 and a pattern output device 13. The quadrupole electromagnet control unit 23 includes a pattern memory 21 and a pattern output device 22.

The method for synchronizing the acceleration cavity 11, the deflection electromagnet 15, and the quadrupole electromagnet 17 with one another will be explained. The clock oscillator 2 generates a clock having a constant frequency, for example, 15 MHz. This clock of 15 MHz is the reference clock. The frequency divider 3 for the high-frequency acceleration cavity divides the reference clock by a predetermined number so as to generate the acceleration cavity clock clka for the high-frequency acceleration cavity. In this situation, when the acceleration cavity clock clka is, for example, 150 kHz, the acceleration cavity clock clka is generated by changing the voltage H and the voltage L of the 15 MHz clock every 50 counts. More specifically, the voltage H ranges over the duration of 50 counts of the 15 MHz clock, and the voltage L ranges over the duration of the following 50 counts of the 15 MHz clock; thus, there is generated a clock whose cycle corresponds to 100 counts of the 15 MHz clock.

Similarly, the frequency divider 4 for the electromagnet divides a clock outputted from the clock oscillator 2 by a predetermined number so as to generate the electromagnet clock clkm for the electromagnet. In this situation, when the electromagnet clock clkm is, for example, 3 kHz, the electromagnet clock clkm is generated by changing the voltage H and the voltage L of the 15 MHz clock every 2500 counts. More specifically, the voltage H ranges over the duration of 2500 counts of the 15 MHz clock, and the voltage L ranges over the duration of the following 2500 counts of the 15 MHz clock; thus, there is generated a clock whose cycle corresponds to 5000 counts of the 15 MHz clock.

Figure 4:
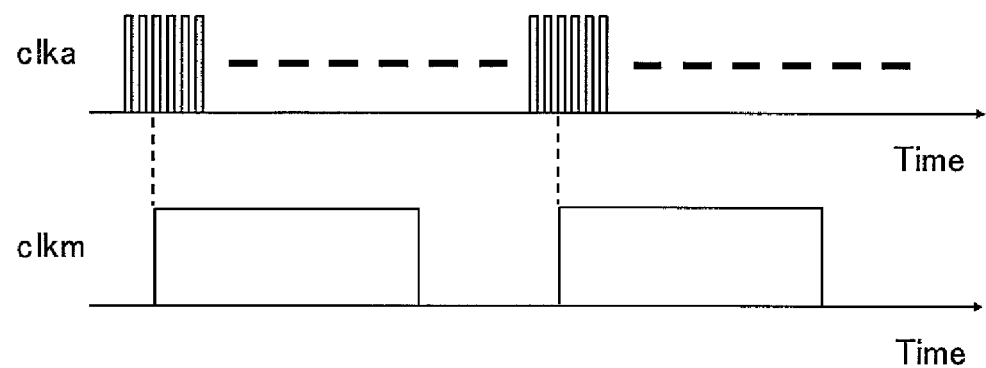
FIG. 4 is a timing chart for explaining an acceleration cavity clock and an electromagnet clock in FIG. 1.

The clock synchronization between the acceleration cavity clock clka and the electromagnet clock clkm will be explained. FIG. 4 is a timing chart for explaining the acceleration cavity clock and the electromagnet clock. As described above, the acceleration cavity clock clka and the electromagnet clock clkm are each generated by dividing the reference clock, and the frequency of the acceleration cavity clock clka is 150 kHz, which is integral multiples of the frequency of the electromagnet clock clkm, i.e., 3 KHz; therefore, as represented in FIG. 4, the rise of the electromagnet clock clkm (a change from the voltage L to the voltage H) definitely coincides with the rise of the acceleration cavity clock clka. In addition, although not represented in FIG. 4, the fall of the electromagnet clock clkm (a change from the voltage H to the voltage L) definitely coincides with the rise of the acceleration cavity clock clka. As described above, the acceleration cavity clock clka and the electromagnet clock clkm are synchronized with each other.

The FR clock generator 6 in the high-frequency control unit 19 calculates the frequency of the acceleration cavity clock clka and multiplies it by a predetermined increase constant (an integer) so that the FR clock clkfr, which is the pattern-output clock for the acceleration cavity 11, is generated. In this Embodiment, it is assumed that the increase constant is, for example, 8. That is to say, it is assumed that the FR clock clkfr is, for example, 1.2 MHz, which is 8 times as high as the frequency of the acceleration cavity clock clka. The FR clock clkfr is a clock for generating a smooth acceleration cavity control signal when the frequency changes and is synchronized with the acceleration cavity clock clka every cycle determined by the increase constant for the FR clock clkfr. The FR clock clkfr is a clock in which a pulse is formed every supplementary time tr, described later.

In Embodiment 1, the FR clock clkfr is reproduced from the acceleration cavity clock clka. The reason why the reference clock is divided so as to generate the acceleration cavity clock clka and then the FR clock clkfr is reproduced from the acceleration cavity clock clka is that because the clock oscillator 2, the frequency divider 3 for the acceleration cavity, and the frequency divider 4 for the electromagnet are formed of a single unit, as the clock generation unit 18, and, in some times, the clock generation unit 18 is provided in a place that is apart from the high-frequency control unit 19, it is required to facilitate the transmission of the FR clock clkfr, which is a high-frequency signal. In the case where the clock generation unit 18 and the high-frequency control unit 19 are provided near to each other, or in the case where they are integrated with each other, the FR clock clkfr may be produced directly from the reference clock.

The operation of the high-frequency control unit 19 will be explained. An acceleration cavity pattern for the acceleration cavity 11 is preliminarily sent from the computer 1 to the pattern memory 5 for the acceleration cavity 11 and is stored in the pattern memory 5. The acceleration cavity pattern is a pattern for setting the frequency value of a high-frequency acceleration voltage corresponding to each cycle of the acceleration cavity clock clka. Because the number of acceleration cavity patterns is not single but plural in accordance with the energy utilized in the particle beam therapy system 51, the operation cycle, the beam intensity, and the like, the pattern memory 5 can store a plurality of acceleration cavity patterns. In the particle beam therapy system 51 according to the scanning irradiation method, approximately 10 sets of acceleration cavity patterns and electromagnet patterns are prepared. In some cases, three acceleration cavity patterns are utilized in a particle beam therapy for a single diseased site. The acceleration cavity patterns are sequentially outputted in synchronization with 150 kHz, which is the acceleration cavity clock clka.

For the purpose of being distinguished from supplementary frequency data, described later, the frequency data of the acceleration cavity pattern stored in the pattern memory 5 will be referred to as "storage frequency data". When receiving the acceleration cavity clock clka, the pattern memory 5 sequentially outputs storage frequency data of the acceleration cavity pattern to the pattern output device 7. In this situation, in order to perform supplementary processing, described later, the pattern memory 5 outputs data that is advanced by one clock from the normal data output. Based on the FR clock clkfr and the storage frequency data of the acceleration cavity pattern inputted from the pattern memory 5, the pattern output device 7 performs supplementary processing and outputs predetermined data (storage frequency data and supplementary frequency data) of the acceleration cavity operation pattern to the synthesizer (digital synthesizer) 8.

Figure 5:
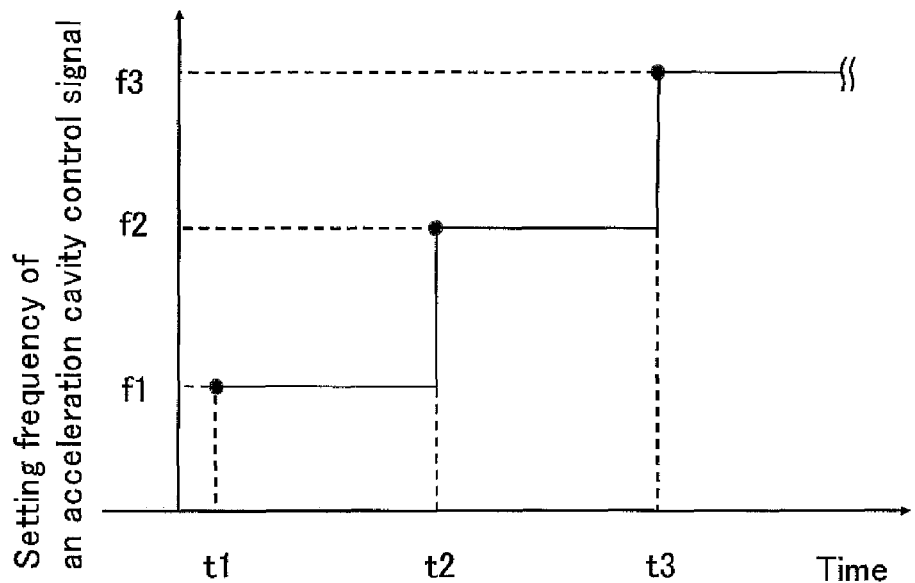
FIG. 5 is a graph representing an example of data output of an acceleration cavity pattern in the case where an acceleration cavity clock is utilized.
Figure 6:
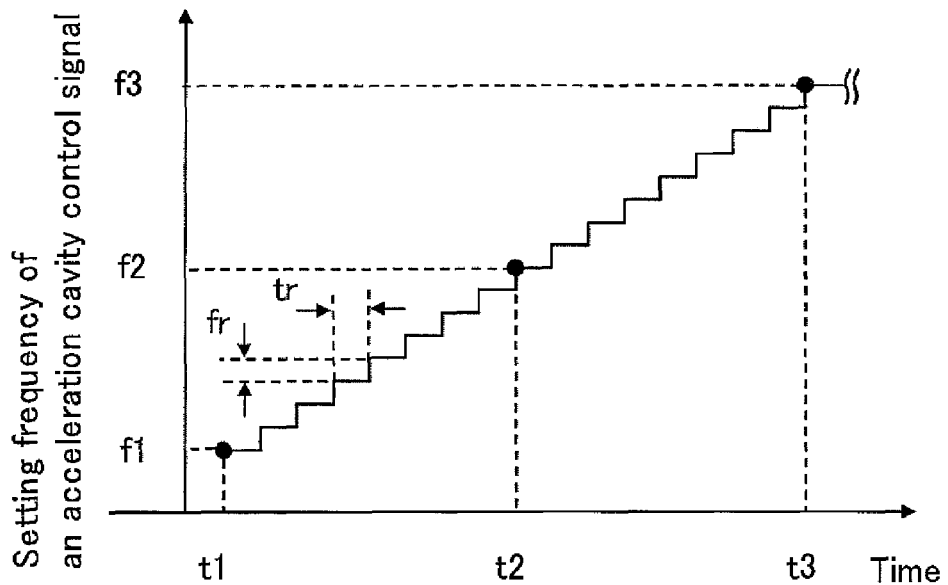
FIG. 6 is a graph representing an example of data output of an acceleration cavity pattern in the case where an FR clock is utilized.

The supplementary processing will be explained. FIG. 5 is a graph representing an example of data output of an acceleration cavity pattern in the case where an acceleration cavity clock is utilized; FIG. 6 is a graph representing an example of data output of an acceleration cavity pattern in the case where an FR clock is utilized. FIG. 5 corresponds to a case where no supplementary processing is performed; FIG. 6 corresponds to a case where supplementary processing is performed. In each of FIGS. 5 and 6, the abscissa denotes the time, and the ordinate denotes the setting frequency of an acceleration cavity control signal. In the case of FIG. 5 representing a case where no supplementary processing is performed, the storage frequency data of the acceleration cavity pattern is outputted from the pattern output device 7 to the synthesizer 8, without applying any supplementary processing to the acceleration cavity pattern that has been stored in the pattern memory 5. In each of FIGS. 5 and 6, the black circle points correspond to the storage frequency data stored in the pattern memory 5. In FIG. 5, when the time, which is a pattern setting time, is t1, the pattern output device 7 outputs data f1 from the acceleration cavity pattern stored in the pattern memory 5. Similarly, when the time is t2, which is the next pattern setting time, the pattern output device 7 outputs data f2, and when the time is t3, which is the further next pattern setting time, the pattern output device 7 outputs data f3. The acceleration cavity pattern is outputted in such a way that the predetermined frequency data is created at the predetermined timing.

Because as an example of data output of the acceleration cavity pattern to which the supplementary processing represented in FIG. 6 is applied, the same acceleration cavity pattern stored in the pattern memory 5 is utilized, the frequency data at a time when the pulse of the acceleration cavity clock clka is inputted is the same. That is to say, in FIG. 6, when the time is t1, which is a pattern setting time, the pattern output device 7 outputs data f1 from the acceleration cavity pattern stored in the pattern memory 5. Similarly, when the time is t2, which is a pattern setting time, the pattern output device 7 outputs data f2, and when the time is t3, which is a pattern setting time, the pattern output device 7 outputs data f3. The acceleration cavity pattern is outputted in such a way that the predetermined frequency data is created at the predetermined timing. However, in addition to the case where the pulse of the acceleration cavity clock clka is inputted, the pattern output device 7 outputs the supplementary frequency data, which is supplemented frequency data, until the pulse of the next acceleration cavity clock clka is inputted. The pattern output device 7 outputs the supplementary frequency data in which a supplementary difference frequency fr is increased or decreased every supplementary time tr.

The supplemented frequency data is outputted each time the FR clock clkfr is inputted. That is to say, the supplementary difference frequency fr corresponds to the frequency of the FR clock clkfr. As described above, the pattern memory 5 outputs the data f2, which is advanced by one clock at the timing of the time t1, to the pattern output device 7. In the case where the supplementary processing is implemented, the pattern output device calculates a supplementary subject frequency difference $\Delta f$, which is the difference between the currently received data f2 and the immediately previously received data f1 and then obtains the supplementary difference frequency fr by dividing the supplementary subject frequency difference $\Delta f$ by a supplementary proportion k, which is the proportion of the FR clock clkfr to the acceleration cavity clock clka. In this example, it is assumed that the FR clock clkfr is 1.2 MHz. Because the acceleration cavity clock clka is 150 kHz and the FR clock clkfr is 1.2 MHz, the supplementary proportion k is 8. Accordingly, the pattern output device 7 outputs the supplementary frequency data, the frequency of which is changed by the supplementary difference frequency fr, which is obtained by dividing the supplementary subject frequency difference $\Delta \omega f$ (f2−f1) by 8, i.e., which is one-eighth of the supplementary subject frequency difference $\Delta f$. The supplementary processing described here is referred to as "linear supplementary processing" or "ramping processing". As far as the supplementary processing is concerned, instead of the linear supplementary processing, there may be implemented a supplement in which an approximation to a curve such as a quadratic curve is performed.

Between pattern setting time points at each of which the storage frequency data of the acceleration cavity pattern is outputted, the pattern output device 7 creates, every supplementary time tr, supplementary frequency data whose frequency is changed by a predetermined supplementary difference frequency fr, and outputs the storage frequency data or the supplementary frequency data each time the FR clock clkfr is inputted; therefore, the stepwise change of the frequency in FIG. 5 can be improved to a smooth change, without increasing pattern data to be stored in the pattern memory 5.

At the times t1, t2, and t3, which are timings of the acceleration cavity clock clka, the pattern output device 7 does not output data to which supplementary processing has been applied in response to the input of the FR clock clkfr; instead, when receiving the output from the pattern memory 5, the pattern output device 7 outputs the immediately previously received frequency data of the acceleration cavity pattern. As a result, high-accuracy synchronous operation can be performed which utilizes the synchronousness between the electromagnet clock clkm and the acceleration cavity clock clka.

The frequency data outputted from the pattern output device 7 is inputted to the synthesizer 8; then, the synthesizer 8 outputs to the AM modulator 9 a high-frequency signal having a frequency indicated by the frequency data. By making multiplication of the output of an unillustrated voltage pattern and the high-frequency signal outputted by the synthesizer 8, the AM modulator 9 performs an AM demodulation and then outputs the AM-modulated AM modulation high-frequency signal to the high-frequency amplifier 10.

The high-frequency amplifier 10 amplifies the AM-modulated AM modulation high-frequency signal and outputs the amplified AM-modulated AM modulation high-frequency signal to the acceleration cavity 11. The high-frequency acceleration voltage outputted from the high-frequency amplifier 10 is applied to the acceleration cavity 11; thus, the high-frequency acceleration voltage is applied to the charged particle beam 31 circulating in the synchrotron, so that the charged particle beam 31 is accelerated.

There will be explained the operations of the deflection electromagnet control unit 20 and the quadrupole electromagnet control unit 23 that control the deflection electromagnet 15 and the quadrupole electromagnet 17, respectively. A deflection electromagnet pattern for the deflection electromagnet 15 is preliminarily sent from the computer 1 to the pattern memory 12 for the deflection electromagnet 15 and is stored in the pattern memory 12. The deflection electromagnet pattern is a pattern for the control input for the deflection electromagnet, i.e., the setting current value corresponding to each cycle of the electromagnet clock clkm. When the electromagnet clock clkm that has been generated by the frequency divider 4 is inputted, the pattern memory 12 outputs the data of the deflection electromagnet pattern for the deflection electromagnet 15 to the pattern output device 13 for the deflection electromagnet 15.

A quadrupole electromagnet pattern for the quadrupole electromagnet 17 is also preliminarily sent from the computer 1 to the pattern memory 21 for the quadrupole electromagnet 17 and is stored in the pattern memory 21. The quadrupole electromagnet pattern is a pattern for the control input for the quadrupole electromagnet, i.e., the setting current value corresponding to each cycle of the electromagnet clock clkm. When the electromagnet clock clkm is inputted, the pattern memory 21 outputs the data of the quadrupole electromagnet pattern for the quadrupole electromagnet 17 to the pattern output device 22 for the quadrupole electromagnet 17.

When receiving the electromagnet clock clkm, the pattern memories 12 and 21 each output the deflection electromagnet pattern and the quadrupole electromagnet pattern, as it is, to the pattern output devices 13 and 22, respectively. The pattern output devices 13 and 22 output the data pieces of the setting current values corresponding to the electromagnet power source 14 for the deflection electromagnet and the electromagnet power source 16 for the quadrupole electromagnet, respectively. The data pieces of the setting current values outputted from the pattern output devices 13 and 22 are inputted to the electromagnet power sources 14 and 16, respectively. The electromagnet power sources 14 and 16 output control currents, corresponding to the data pieces of the setting current values, that are applied to the deflection electromagnet 15 and the quadrupole electromagnet 17, respectively. The deflection electromagnet 15 applies a magnetic field to the charged particle beam 31 so that the charged particle beam 31 circulates on a predetermined orbit in the vacuum duct 24; the quadrupole electromagnet 17 applies a magnetic field to the charged particle beam 31 so that the size of the charged particle beam 31 becomes a predetermined one.

As described above, because the electromagnets corresponding to the electromagnet power sources 14 and 16 are coils including an iron core, these electromagnets are likely to have a reactance component of a large time constant; therefore, even when the data of the setting current value for the electromagnet pattern such as the deflection electromagnet pattern or the quadrupole electromagnet pattern changes in a step manner in the cycle of 3 kHz, the energizing currents (control currents) supplied from the electromagnet power sources 14 and 16 to the corresponding electromagnets do not change rapidly, unlike the case with the acceleration cavity 11, but change in an appropriately smooth manner.

In the charged particle accelerator 54 according to Embodiment 1, the timings of the change in the supplementarily processed high-frequency acceleration voltage for the acceleration cavity 11 and the timing of the change in the energizing current for the deflection electromagnet 15 or the quadrupole electromagnet 17 are made to coincide with each other, i.e., synchronized with each other; thus, stable beam acceleration can be achieved.

Next, the data transfer time will be considered in which the computer 1 transfers data to the high-frequency control unit 19, the deflection electromagnet control unit 20, and the quadrupole electromagnet control unit 23. In the case where the acceleration cavity clock clka is 150 kHz and the electromagnet clock clkm is 3 kHz, and 20 sets each of the acceleration cavity patterns and the electromagnet patterns are data-transferred from the computer 1 to the high-frequency control unit 19, the deflection electromagnet control unit 20, and the quadrupole electromagnet control unit 23, the data transfer time is, for example, approximately 4 seconds. In the charged particle accelerator 54 according to Embodiment 1, the acceleration cavity 11 is controlled based on the pulse input of the 1.2 MHz FR clock clkfr and the frequency data that is outputted from the pattern memory 5 every outputting timing thereof, and the control of the deflection electromagnet 15 and the quadrupole electromagnet 17 is implemented in such a way as to follow the control of the acceleration cavity 11. In the case of the charged particle accelerator (a comparison-subject charged particle accelerator) in Patent Document 1 in which the acceleration cavity and the electromagnet are operated only with a comparison-subject T-clock, the data transfer time can be estimated as stated below.

In the comparison-subject charged particle accelerator, the acceleration cavity pattern and the electromagnet pattern are transferred at 1.2 MHz; therefore, the data amount of the acceleration cavity pattern is 8 (=1.2 M/150 k) times as much as that in Embodiment 1, and the respective data amounts of the deflection electromagnet pattern and the quadrupole electromagnet pattern are 400 (=1.2 M/3 k) times as much as those in Embodiment 1. In this situation, letting A denote the data amount of the deflection electromagnet pattern in Embodiment 1, the respective data amounts of the deflection electromagnet pattern, the quadrupole electromagnet pattern, and the acceleration cavity pattern in Embodiment 1 are A, A, and 50A (=A×(150 k/3 k)). The respective data amounts of the deflection electromagnet pattern, the quadrupole electromagnet pattern, and the acceleration cavity pattern in the comparison-subject charged particle accelerator are 400A, 400A, and 400A (=8×50A). Assuming that there exist 20 sets of electromagnets, the total data amounts of the electromagnet pattern and the acceleration cavity pattern in the charged particle accelerator 54 in Embodiment 1 is 70A (=20A+50A). In contrast, the total data amounts of the electromagnet pattern and the acceleration cavity pattern in the comparison-subject charged particle accelerator is 8400A (=20×400A+400A). Accordingly, the data transfer time in the comparison-subject charged particle accelerator is 8400/70 times, i.e., 120 times as long as data transfer time in the charged particle accelerator 54 in Embodiment 1, which is 8 (=4×120/60) minutes.

The data transfer time in the comparison-subject charged particle accelerator is a long time of approximately 8 minutes per operation parameter; for example, when patients are changed, it takes a long time to transfer the data of the acceleration cavity pattern and the electromagnet pattern matched to the new patient, whereby the number of patients to whom particle beam therapy can be applied in a single day extremely decreases. Even when there are taken measures in which pattern data to be utilized in the therapy is preliminarily downloaded, a long time of approximately 8 minutes is required for each operation parameter, when some sort of trouble happens and the acceleration cavity pattern and the electromagnet pattern are transferred again; thus, after a patient is taken down from the treatment table and waits for a time, the positioning for the patient is implemented again, whereby there is posed a problem that the particle beam therapy stagnates. In general, not a single but a plurality of operation parameters are utilized in the therapy; in this case, the difference between the data transfer time in Embodiment 1 and the data transfer time in the comparison-subject charged particle accelerator becomes further large, whereby the importance of the problem increases.

Unlike the comparison-subject charged particle accelerator, the data transfer time in the charged particle accelerator 54 according to Embodiment 1 is approximately 4 seconds; even when patients are changed or even when due to a trouble, the acceleration cavity pattern and the electromagnet pattern are transferred again, the data transfer time is approximately 4 seconds and hence the number of patients to whom the particle beam therapy can be applied in a single day does not extremely decrease; therefore, there is posed no problem that the particle beam therapy stagnates. Accordingly, in the particle beam therapy system 51 provided with the charged particle accelerator 54 according to Embodiment 1, the data transfer time for the acceleration cavity pattern and the electromagnet pattern can extremely be shortened compared with conventional particle beam therapy systems; therefore, the particle beam therapy can efficiently be implemented.

In the charged particle accelerator 54 according to Embodiment 1, the acceleration cavity clock clka and the electromagnet clock clkm are synchronized with each other but have different frequencies, so that the data amount of the electromagnet pattern such as a deflection electromagnet pattern or the quadrupole electromagnet pattern can be reduced. Accordingly, the total data amount of the acceleration cavity pattern and the electromagnet pattern can be reduced, whereby the time for the communication of pattern data between the computer 1 and the pattern memories 5, 12, and 21 can be reduced. In Embodiment 1, the acceleration cavity clock clka and the electromagnet clock clkm are generated by dividing the reference clock; however, it may be allowed that the acceleration cavity clock clka is generated by dividing the reference clock and then the electromagnet clock clkm is generated by dividing the acceleration cavity clock clka.

In the charged particle accelerator 54 according to Embodiment 1, from the acceleration cavity clock clka, the FR clock clkfr having a higher frequency is generated, and from the acceleration cavity pattern stored in the pattern memory 5 for the acceleration cavity 11, the acceleration cavity operation pattern having a further high temporal resolution is generated by the pattern output device 7 for the acceleration cavity 11 and is outputted to the synthesizer 8, so that the data amount of the acceleration cavity pattern can also be reduced.

In the charged particle accelerator 54 according to Embodiment 1, even when the data amount of the electromagnet pattern such as the deflection electromagnet pattern or the quadrupole electromagnet pattern is reduced, the energizing currents supplied from the electromagnet power sources 14 and 16 to the corresponding electromagnets change in an appropriately smooth manner; therefore, by synchronizing the change in the high-frequency acceleration voltage with the change in the energizing currents for the deflection electromagnet 15 and the quadrupole electromagnet 17, stable beam acceleration can be achieved. Furthermore, even when the data amount of the acceleration cavity pattern is reduced, the acceleration cavity operation pattern having a temporal resolution higher than that of the acceleration cavity pattern is generated and based on the acceleration cavity operation pattern, a high-frequency acceleration voltage is applied to the acceleration cavity 11; therefore, the change in the high-frequency acceleration voltage can be synchronized with the change in the energizing currents for the deflection electromagnet 15 and the quadrupole electromagnet 17, whereby stable beam acceleration can be achieved.

In the charged particle accelerator 54 according to Embodiment 1, unlike a charged particle accelerator utilizing B-clock and T-clock, the acceleration cavity clock clka and the electromagnet clock clkm are generated only through T-clock; therefore, the system configuration of the charged particle accelerator 54 can be simplified compared with conventional systems. In the charged particle accelerator 54 according to Embodiment 1, unlike the charged particle accelerator disclosed in Patent Document 1 in which the acceleration cavity and the electromagnet are operated only through T-clock, the total data amount of the acceleration cavity pattern and the electromagnet pattern is reduced; therefore, because the data of the acceleration cavity pattern and the electromagnet pattern can readily be managed, the system for the data communication between the computer 1 and the high-frequency control unit 19, the deflection electromagnet control unit 20, or the quadrupole electromagnet control unit 23 can also be simplified compared with conventional systems.

The charged particle accelerator 54 according to Embodiment 1 includes the vacuum duct 24 through which the charged particle beam 31 passes; the acceleration cavity 11 that accelerates the charged particle beam 31 passing through the vacuum duct 24; the deflection electromagnet 15 that deflects the charged particle beam 31 passing through the vacuum duct 24; and the accelerator control apparatus 25 that controls the acceleration cavity 11 and the deflection electromagnet 15. The accelerator control apparatus 25 includes the clock generation unit 18 that generates the acceleration cavity clock clka and the electromagnet clock clkm that is synchronized with the acceleration cavity clock clka and has a frequency lower than the frequency of the acceleration cavity clock clka; the high-frequency control unit 19 that controls the acceleration cavity 11, based on the acceleration cavity pattern stored in the first pattern memory 5 and the acceleration cavity clock clka; and the deflection electromagnet control unit 20 that controls the deflection electromagnet 15, based on the deflection electromagnet pattern stored in the second pattern memory 12 and the electromagnet clock clkm. As a result, it is made possible to make the data amount of the deflection electromagnet pattern smaller than that of the acceleration cavity pattern; thus, the time for the communication of the pattern data with the accelerator can be shortened.

The particle beam therapy system 51 according to Embodiment 1 includes the beam generation apparatus 52 that generates the charged particle beam 31 and accelerates it by means of the accelerator 54; the beam transport system 59 that transports the charged particle beam 31 accelerated by the charged particle accelerator 54; and the particle beam irradiation apparatus 58 that irradiates the charged particle beam 31 transported by the beam transport system 59 onto the irradiation subject 45. The charged particle accelerator 54 is provided with the vacuum duct through which the charged particle beam 31 passes; the acceleration cavity 11 that accelerates the charged particle beam passing through the vacuum duct 24; the deflection electromagnet 15 that deflects the charged particle beam 31 passing through the vacuum duct 24; and the accelerator control apparatus 25 that controls the acceleration cavity 11 and the deflection electromagnet 15. The accelerator control apparatus 25 includes the clock generation unit 18 that generates the acceleration cavity clock clka and the electromagnet clock clkm that is synchronized with the acceleration cavity clock clka and has a frequency lower than the frequency of the acceleration cavity clock clka; the high-frequency control unit 19 that controls the acceleration cavity 11, based on the acceleration cavity pattern stored in the first pattern memory 5 and the acceleration cavity clock clka; and the deflection electromagnet control unit 20 that controls the deflection electromagnet 15, based on the deflection electromagnet pattern stored in the second pattern memory 12 and the electromagnet clock clkm. As a result, it is made possible to make the data amount of the deflection electromagnet pattern smaller than that of the acceleration cavity pattern; thus, the time for the communication of the pattern data with the accelerator can be shortened. Accordingly, in the particle beam therapy system 51 provided with the charged particle accelerator 54 according to Embodiment 1, the data transfer time for the acceleration cavity pattern and the electromagnet pattern can extremely be shortened compared with conventional particle beam therapy systems; therefore, the particle beam therapy can efficiently be implemented.

The example has been explained in which the FR clock generator 6 calculates the frequency of the acceleration cavity clock clka and multiplies it by a predetermined increase constant (an integer) so that the FR clock clkfr is generated; however, it may be allowed that the FR clock generator 6 divides the reference clock so as to generate the FR clock clkfr.

Embodiment 2

Figure 7:
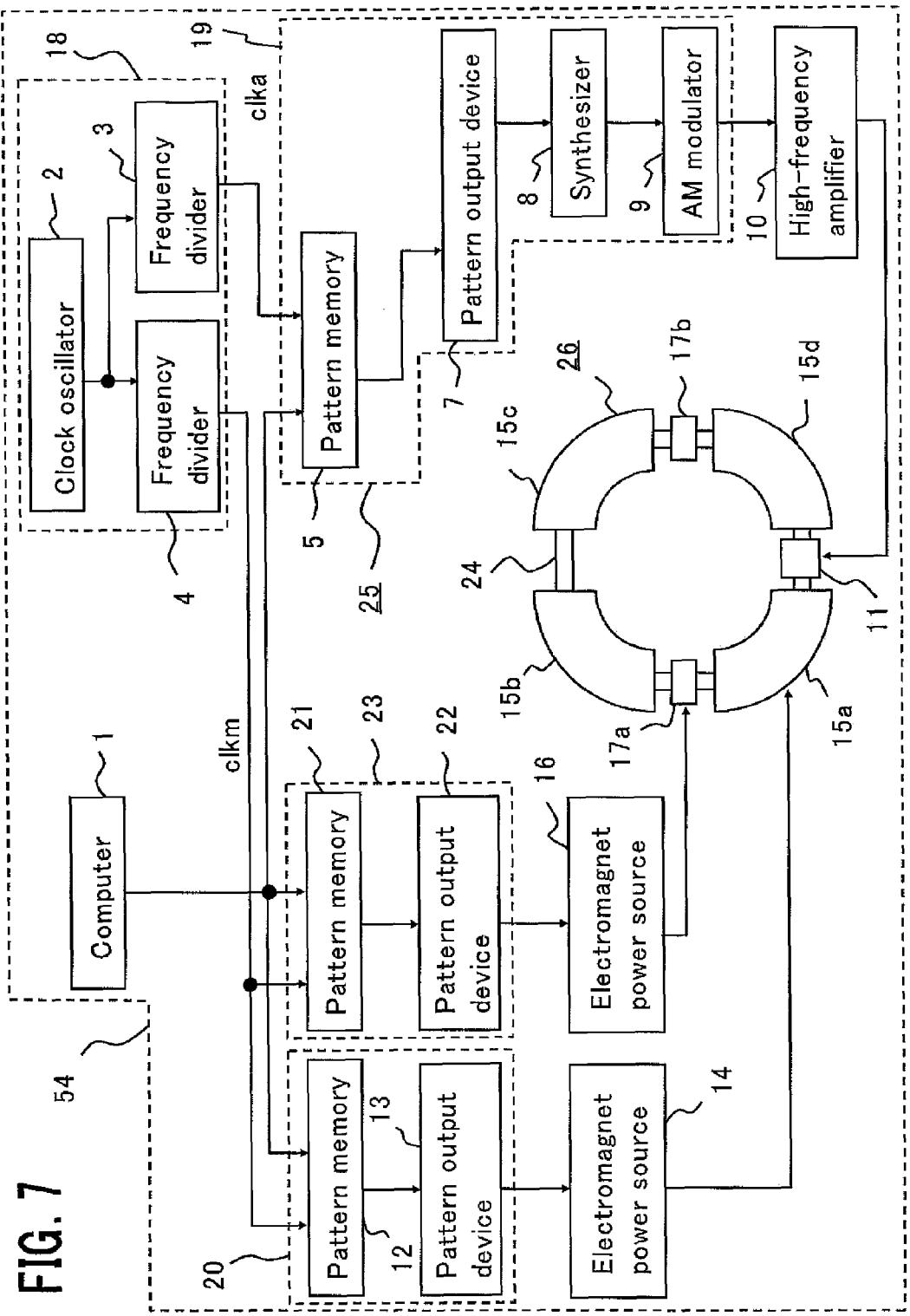
FIG. 7 is a diagram illustrating the configuration of a charged particle accelerator according to Embodiment 2 of the present invention.

FIG. 7 is a diagram illustrating the configuration of a charged particle accelerator according to Embodiment 2 of the present invention. A charged particle accelerator 54 according to Embodiment 2 is different from the charged particle accelerator 54 according to Embodiment 1 in that the FR clock generator 6 is eliminated and the frequency of the acceleration cavity clock clka and the amount of the frequency data of the acceleration cavity pattern stored in the pattern memory 5 are different. In this Description, there will be explained an example in which the outputting frequency of the frequency data explained in Embodiment 1 is the same.

In Embodiment 1, the pattern output device 7 outputs the frequency data of the acceleration cavity pattern to the synthesizer 8, by use of the FR clock clkfr of 1.2 MHz. Thus, in Embodiment 2, the frequency divider 3 generates the acceleration cavity clock clka of 1.2 MHz. Specifically, in Embodiment 2, a reference clock of 12 MHz is generated; the frequency divider 3 divides the reference clock generated by the clock oscillator 2 so as to generate the acceleration cavity clock clka of 1.2 MHz, which is one-hundredth of the frequency of the reference clock. As explained in Embodiment 1, the acceleration cavity clock clka and the electromagnet clock clkm are each generated by dividing a single reference clock, and the frequency of the acceleration cavity clock clka is 1.2 MHz, which can be obtained by multiplying the frequency of the electromagnet clock clkm, i.e., 3 KHz; therefore, the clocks are synchronized with each other.

Next, the operation of the high-frequency control unit 19 according to Embodiment 2 will be explained. An acceleration cavity pattern for the acceleration cavity 11 is preliminarily sent from the computer 1 to the pattern memory 5 and is stored in the pattern memory 5. Because the frequency of the acceleration cavity clock clka is changed from 150 kHz to 1.2 MHz, the amount of the frequency data of the acceleration cavity pattern stored in the pattern memory 5 increases up to 8 times (=1.2 M/150 k). The acceleration cavity patterns are sequentially outputted in synchronization with 1.2 MHz, which is the acceleration cavity clock clka.

Figure 8:
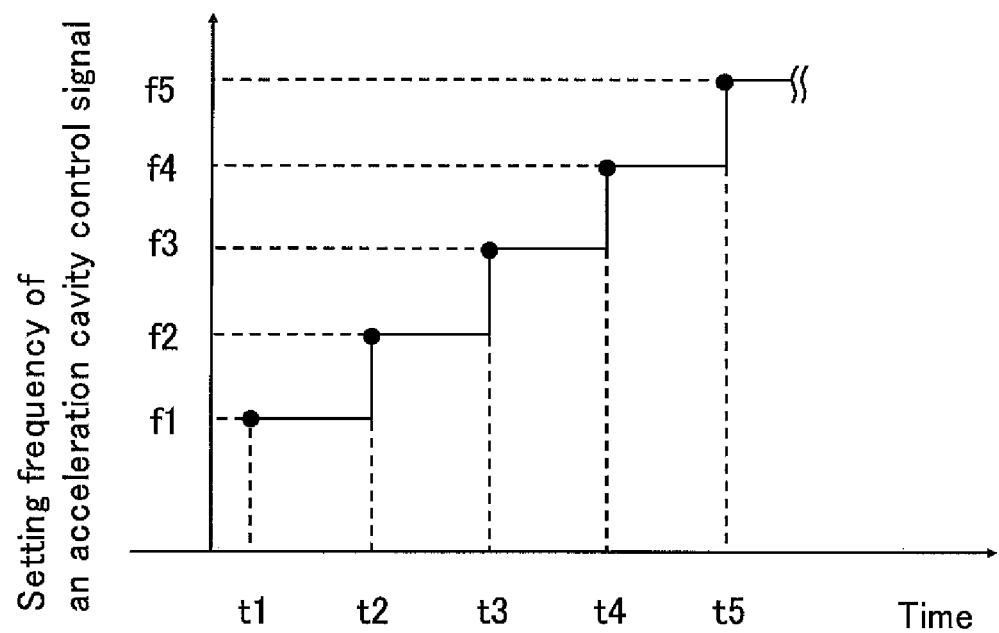
FIG. 8 is a graph representing an example of data output of an acceleration cavity pattern according to Embodiment 2 of the present invention.

FIG. 8 is a graph representing an example of data output of an acceleration cavity pattern according to Embodiment 2 of the present invention. In FIG. 8, the abscissa denotes the time, and the ordinate denotes the setting frequency of an acceleration cavity control signal. In FIG. 8, the black circle points correspond to the frequency data stored in the pattern memory 5. In FIG. 8, when the time is t1, the pattern output device 7 outputs data f1 from the acceleration cavity pattern stored in the pattern memory 5. Similarly, when the times are t2, t3, t4, and t5, the pattern output device 7 outputs data f2, f3, f4, and f5, respectively. The acceleration cavity pattern is outputted in such a way that the predetermined frequency data is created at the predetermined timing, i.e., at the pulse input timing of the acceleration cavity clock clka.

When receiving the acceleration cavity clock clka, the pattern memory 5 sequentially outputs the data of the acceleration cavity pattern to the pattern output device 7. The pattern output device 7 outputs the frequency data of the acceleration cavity pattern to the synthesizer 8. Based on the frequency data, the synthesizer 8 outputs a high-frequency signal having a frequency indicated by the frequency data to the AM modulator 9. By making multiplication of the output of an unillustrated voltage pattern and the high-frequency signal outputted by the synthesizer 8, the AM modulator 9 performs an AM demodulation and then outputs the AM-modulated AM modulation high-frequency signal to the high-frequency amplifier 10.

The high-frequency amplifier 10 amplifies the AM-modulated AM modulation high-frequency signal and outputs the amplified AM-modulated AM modulation high-frequency signal to the acceleration cavity 11. The high-frequency acceleration voltage outputted from the high-frequency amplifier 10 is applied to the acceleration cavity 11; thus, the high-frequency acceleration voltage is applied to the charged particle beam 31 circulating in the synchrotron, so that the charged particle beam 31 is accelerated. The operations of the deflection electromagnet control unit 20 and the quadrupole electromagnet control unit 23 that control the deflection electromagnet 15 and the quadrupole electromagnet 17, respectively, are the same as those thereof in Embodiment 1.

The data transfer time from the computer 1 to the high-frequency control unit 19, the deflection electromagnet control unit 20, and the quadrupole electromagnet control unit 23 in the charged particle accelerator 54 according to Embodiment 2 will be compared with the data transfer time in the charged particle accelerator 54 according to Embodiment 1. As described above, in the charged particle accelerator 54 according to Embodiment 1, the acceleration cavity clock clka is 150 kHz and the electromagnet clock clkm is 3 kHz, and when 20 sets each of the acceleration cavity patterns and the electromagnet patterns are data-transferred from the computer 1 to the high-frequency control unit 19, the deflection electromagnet control unit 20, and the quadrupole electromagnet control unit 23, the data transfer time is approximately 4 seconds. In the charged particle accelerator 54 according to Embodiment 2, the acceleration cavity clock clka is 1.2 MHz, which is 8 times as high as the acceleration cavity clock clka in Embodiment 1. In this situation, letting A denote the data amount of the electromagnet pattern according to Embodiment 1, the data amount of the acceleration cavity pattern is 400A (=8×50A). Therefore, the total data amounts of the electromagnet pattern, the quadrupole electromagnet pattern, and the acceleration cavity pattern in the charged particle accelerator 54 according to Embodiment 2 is 420A (=20×A+400A).

The data transfer time in the charged particle accelerator 54 according to Embodiment 2 is 420/70 times, i.e., 6 times as long as data transfer time in the charged particle accelerator 54 according to Embodiment 1, which is 24 (=4×6) seconds. The data transfer time in the charged particle accelerator 54 according to Embodiment 2 is longer than the data transfer time in the charged particle accelerator 54 according to Embodiment 1; however, it can be shortened compared with the data transfer time (8 minutes) in the comparison-subject charged particle accelerator.

Unlike the comparison-subject charged particle accelerator, the data transfer time in the charged particle accelerator 54 according to Embodiment 2 is approximately 24 seconds; therefore, it is not extremely long compared with the positioning time for a patient. Even when patients are changed or even when due to a trouble, the acceleration cavity pattern and the electromagnet pattern are transferred again, the data transfer time in the charged particle accelerator 54 according to Embodiment 2 is approximately 24 seconds and hence the number of patients to whom the particle beam therapy can be applied in a single day does not extremely decrease; therefore, there is posed no problem that the particle beam therapy stagnates. Accordingly, in the particle beam therapy system provided with the charged particle accelerator according to Embodiment 2, the data transfer time for the acceleration cavity pattern and the electromagnet pattern can extremely be shortened compared with conventional particle beam therapy systems; therefore, the particle beam therapy can efficiently be implemented.

In the charged particle accelerator 54 according to Embodiment 2, the acceleration cavity clock clka and the electromagnet clock clkm are synchronized with each other but have different frequencies, so that the data amount of the electromagnet pattern such as a deflection electromagnet pattern or the quadrupole electromagnet pattern can be reduced. Accordingly, the total data amount of the acceleration cavity pattern and the electromagnet pattern can be reduced, whereby the time for the communication of pattern data between the computer and the pattern memories of the accelerator can be reduced.

In the charged particle accelerator 54 according to Embodiment 2, as is the case with Embodiment 1, even when the data amount of the electromagnet pattern such as the deflection electromagnet pattern or the quadrupole electromagnet pattern is reduced, the energizing currents supplied from the electromagnet power sources 14 and 16 to the corresponding electromagnets change in an appropriately smooth manner; therefore, by synchronizing the change in the high-frequency acceleration voltage with the change in the energizing currents for the deflection electromagnet 15 and the quadrupole electromagnet 17, stable beam acceleration can be achieved.

In each of Embodiments 1 and 2, an example has been explained in which the computer 1 is provided in addition to the irradiation control computer 39; however, it may be allowed that the computer is not provided and the irradiation control computer 39 implements the processing to be performed by the computer 1.

DESCRIPTION OF REFERENCE NUMERALS

2: clock oscillator
3: frequency divider
4: frequency divider
5: pattern memory
6: FR clock generator
7: pattern output device
11: acceleration cavity
12: pattern memory
15, 15a, 15b, 15c, 15d: deflection electromagnet
18: clock generation unit
19: high-frequency control unit
20: deflection electromagnet control unit
24: vacuum duct
25: accelerator control apparatus
31: charged particle beam
45: irradiation subject
51: particle beam therapy system
52: beam generation apparatus
54: charged particle accelerator
58, 58a, 58b: particle beam irradiation apparatus
59: beam transport system clka: acceleration cavity clock
clkm: electromagnet clock
clkfr: FR clock

The invention claimed is:

1. A charged particle accelerator that accelerates a charged particle beam to be irradiated onto an irradiation subject by a particle beam irradiation apparatus, the charged particle accelerator comprising:
a vacuum duct through which the charged particle beam passes;
an acceleration cavity that accelerates the charged particle beam passing through the vacuum duct;
a deflection electromagnet that deflects the charged particle beam passing through the vacuum duct; and
an accelerator control apparatus that controls the acceleration cavity and the deflection electromagnet, wherein the accelerator control apparatus includes a clock generation unit that generates an acceleration cavity clock and an electromagnet clock that is synchronized with the acceleration cavity clock and has a frequency lower than the frequency of the acceleration cavity clock; a high-frequency control unit that controls the acceleration cavity, based on an acceleration cavity pattern stored in a first pattern memory and the acceleration cavity clock; and a deflection electromagnet control unit that controls the deflection electromagnet, based on a deflection electromagnet pattern stored in a second pattern memory and the electromagnet clock.

2. The charged particle accelerator according to claim 1, wherein the clock generation unit includes a clock oscillator that generates a reference clock for generating the acceleration cavity clock and the electromagnet clock; a first frequency divider that divides the reference clock so as to generate the acceleration cavity clock; and a second frequency divider that divides the reference clock so as to generate the electromagnet clock.

3. The charged particle accelerator according to claim 1, wherein the clock generation unit generates the acceleration cavity clock whose frequency is an integer times as high as the frequency of the electromagnet clock.

4. The charged particle accelerator according to claim 1, wherein between pattern setting time points at each of which storage frequency data of the acceleration cavity pattern is outputted, the high-frequency control unit creates, every supplementary time, supplementary frequency data whose frequency is changed by a predetermined supplementary difference frequency, and controls the acceleration cavity based on the storage frequency data and the supplementary frequency data.

5. The charged particle accelerator according to claim 4, wherein the high-frequency control unit creates the supplementary frequency data by applying linear supplementary processing to the respective storage frequency data pieces at two of the continual pattern setting time points.

6. The charged particle accelerator according to claim 4, wherein the high-frequency control unit includes an FR clock generator that generates an FR clock that is synchronized with the acceleration cavity clock and in which a pulse is formed every supplementary time; and a pattern output device that outputs the storage frequency data or the supplementary frequency data each time the FR clock is inputted thereto.

7. The charged particle accelerator according to claim 6, wherein the FR clock generator calculates the cycle of the acceleration cavity clock and generates the FR clock in such a way as to integer-multiply the acceleration cavity clock by a predetermined increase constant.

8. The charged particle accelerator according to claim 6, wherein the FR clock generator generates the FR clock from a reference clock for generating the acceleration cavity clock or from the acceleration cavity clock.

9. The charged particle accelerator according to claim 8, wherein the FR clock generator generates the FR clock whose frequency is an integer times as high as the frequency of the acceleration cavity clock.

10. A particle beam therapy system comprising:
a beam generation apparatus that generates a charged particle beam and accelerates the charged particle beam by means of a charged particle accelerator;
a beam transport system that transports a charged particle beam accelerated by the charged particle accelerator; and
a particle beam irradiation apparatus that irradiates a charged particle beam transported by the beam transport system onto an irradiation subject, wherein the charged particle accelerator is the charged particle accelerator according to claim 1.

11. The charged particle accelerator according to claim 2, wherein the clock generation unit generates the acceleration cavity clock whose frequency is an integer times as high as the frequency of the electromagnet clock.

12. The charged particle accelerator according to claim 2, wherein between pattern setting time points at each of which storage frequency data of the acceleration cavity pattern is outputted, the high-frequency control unit creates, every supplementary time, supplementary frequency data whose frequency is changed by a predetermined supplementary difference frequency, and controls the acceleration cavity based on the storage frequency data and the supplementary frequency data.

13. The charged particle accelerator according to claim 3, wherein between pattern setting time points at each of which storage frequency data of the acceleration cavity pattern is outputted, the high-frequency control unit creates, every supplementary time, supplementary frequency data whose frequency is changed by a predetermined supplementary difference frequency, and controls the acceleration cavity based on the storage frequency data and the supplementary frequency data.

14. The charged particle accelerator according to claim 5, wherein the high-frequency control unit includes an FR clock generator that generates an FR clock that is synchronized with the acceleration cavity clock and in which a pulse is formed every supplementary time; and a pattern output device that outputs the storage frequency data or the supplementary frequency data each time the FR clock is inputted thereto.

15. A particle beam therapy system comprising:
a beam generation apparatus that generates a charged particle beam and accelerates the charged particle beam by means of a charged particle accelerator;
a beam transport system that transports a charged particle beam accelerated by the charged particle accelerator; and
a particle beam irradiation apparatus that irradiates a charged particle beam transported by the beam transport system onto an irradiation subject, wherein the charged particle accelerator is the charged particle accelerator according to claim 2.

16. A particle beam therapy system comprising:
a beam generation apparatus that generates a charged particle beam and accelerates the charged particle beam by means of a charged particle accelerator;

a beam transport system that transports a charged particle beam accelerated by the charged particle accelerator; and a particle beam irradiation apparatus that irradiates a charged particle beam transported by the beam transport system onto an irradiation subject, wherein the charged particle accelerator is the charged particle accelerator according to claim 3.

17. A particle beam therapy system comprising:

a beam generation apparatus that generates a charged particle beam and accelerates the charged particle beam by means of a charged particle accelerator;

a beam transport system that transports a charged particle beam accelerated by the charged particle accelerator; and a particle beam irradiation apparatus that irradiates a charged particle beam transported by the beam transport system onto an irradiation subject, wherein the charged particle accelerator is the charged particle accelerator according to claim 4.

18. A particle beam therapy system comprising:

a beam generation apparatus that generates a charged particle beam and accelerates the charged particle beam by means of a charged particle accelerator;

a beam transport system that transports a charged particle beam accelerated by the charged particle accelerator; and a particle beam irradiation apparatus that irradiates a charged particle beam transported by the beam transport system onto an irradiation subject, wherein the charged particle accelerator is the charged particle accelerator according to claim 5.

19. A particle beam therapy system comprising:

a beam generation apparatus that generates a charged particle beam and accelerates the charged particle beam by means of a charged particle accelerator;

a beam transport system that transports a charged particle beam accelerated by the charged particle accelerator; and a particle beam irradiation apparatus that irradiates a charged particle beam transported by the beam transport system onto an irradiation subject, wherein the charged particle accelerator is the charged particle accelerator according to claim 6.

20. A particle beam therapy system comprising:

a beam generation apparatus that generates a charged particle beam and accelerates the charged particle beam by means of a charged particle accelerator;

a beam transport system that transports a charged particle beam accelerated by the charged particle accelerator; and a particle beam irradiation apparatus that irradiates a charged particle beam transported by the beam transport system onto an irradiation subject, wherein the charged particle accelerator is the charged particle accelerator according to claim 7.

* * * * *